(12) United States Patent
Anuszewski et al.

(10) Patent No.: US 8,583,451 B2
(45) Date of Patent: Nov. 12, 2013

(54) CONTEXT INFORMATION PROCESSING SYSTEM USED FOR ACCESSING MEDICAL DATA

(75) Inventors: David Anuszewski, Pottstown, PA (US); Oladimeji Okewole, Lansdowne, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 2197 days.

(21) Appl. No.: 11/556,356

(22) Filed: Nov. 3, 2006

(65) Prior Publication Data

US 2007/0185738 A1    Aug. 9, 2007

Related U.S. Application Data

(60) Provisional application No. 60/733,610, filed on Nov. 4, 2005.

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC .......................................................... 705/2, 3
See application file for complete search history.

(56) References Cited

U.S. PATENT DOCUMENTS

| 5,963,136 | A | 10/1999 | O'Brien | |
|---|---|---|---|---|
| 6,260,049 | B1 | 7/2001 | Fitzgerald et al. | |
| 6,380,858 | B1 * | 4/2002 | Yarin et al. | 340/573.1 |
| 6,816,075 | B2 | 11/2004 | Grunes et al. | |
| 2002/0038392 | A1 | 3/2002 | De La Huerga | |
| 2002/0190862 | A1 | 12/2002 | Berquist et al. | |
| 2004/0034650 | A1 | 2/2004 | Springer | |
| 2005/0148890 | A1 | 7/2005 | Hastings | |
| 2006/0047538 | A1 * | 3/2006 | Condurso et al. | 705/3 |
| 2006/0111941 | A1 | 5/2006 | Blom | |
| 2006/0167367 | A1 | 7/2006 | Stanczak et al. | |
| 2006/0180659 | A1 | 8/2006 | Loffredo et al. | |
| 2006/0236373 | A1 * | 10/2006 | Graves et al. | 726/3 |

FOREIGN PATENT DOCUMENTS

WO    WO 03/009224 A    1/2003

OTHER PUBLICATIONS

International Search Report (May 11, 2007).

* cited by examiner

*Primary Examiner* — Robert Morgan
*Assistant Examiner* — Maroun Kanaan
(74) *Attorney, Agent, or Firm* — Joshua B Ryan

(57) ABSTRACT

A context information processing system used for accessing medical data includes an acquisition processor for acquiring configuration information indicating a type of a particular patient identification tag reader device of a plurality of different types of tag reader device and a format of patient identification data used by the particular patient identification tag reader device. An interpreter processes patient identification data received from the particular patient identification tag reader device using the received configuration information to provide a particular patient identifier. A context processor updates a record indicating that a current patient context, including a patient identifier, is compatible with the particular patient identifier.

20 Claims, 2 Drawing Sheets

US 8,583,451 B2

CONTEXT INFORMATION PROCESSING SYSTEM USED FOR ACCESSING MEDICAL DATA

This application derives priority from Provisional Patent Application No. 60/733,610, filed on Nov. 4, 2005.

FIELD OF THE INVENTION

The present invention relates generally to the field of data processing, and more particularly to a context information processing system for the acquisition and characterization of data, and in particular medical data, contained within remotely located discrete identification media.

BACKGROUND OF THE INVENTION

A patient in a healthcare facility is typically fitted with some type of device, such as a bracelet or other device, in order to positively identify that patient while they are receiving services. Existing remote patient management systems frequently utilize one of a plurality of identification technologies, for example, either barcode or radio frequency identification (RFID) tags, to accomplish patient identification and selection. Both the hardware and software deployed when implementing such a system are typically dedicated to the operation of a selected type of identification device using a corresponding protocol. In those situations where the management system software application does support both protocols, such support is achieved by providing alternative implementations for the respective technologies and protocols. In other words, the system user determines the technology to be deployed for patient selection prior to deployment of a patient management solution. For software vendors this requirement limits the available universe of potential healthcare provider customers to only those that have an implementation targeted at the identification technology that has already been chosen by the potential customer.

In those situations where a healthcare provider chooses to switch identification technology after an original software application is deployed, a software upgrade is mandatory, or if the patient management solution does not support the newly selected patient identification technology, a new patient management solution is selected or designed and implemented. From the perspective of an application software provider, the customer either targets a specific patient selection technology or incurs the cost of an alternative implementation. A system according to the principles of the present invention addresses these issues and their related problems.

BRIEF SUMMARY OF THE INVENTION

In accordance with principles of the present invention, a context information processing system used for accessing medical data includes an acquisition processor for acquiring configuration information indicating a type of a particular patient identification tag reader device of a plurality of different types of tag reader device and a format of patient identification data used by the particular patient identification tag reader device. An interpreter processes patient identification data received from the particular patient identification tag reader device using the received configuration information to provide a particular patient identifier. A context processor updates a record indicating that a current patient context, including a patient identifier, is compatible with the particular patient identifier.

DETAILED DESCRIPTION OF THE INVENTION

A processor, as used herein, operates under the control of an executable application to (a) receive information from an input information device, (b) process the information by manipulating, analyzing, modifying, converting and/or transmitting the information, and/or (c) route the information to an output information device. A processor may use, or comprise the capabilities of, a controller or microprocessor, for example. The processor may operate with a display processor or generator. A display processor or generator is a known element for generating signals representing display images or portions thereof. A processor and a display processor comprises any combination of, hardware, firmware, and/or software.

An executable application, as used herein, comprises code or machine readable instructions for conditioning the processor to implement predetermined functions, such as those of an operating system, a context acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A user interface (UI), as used herein, comprises one or more display images, generated by the display processor under the control of the processor. The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to the processor. The processor, under control of the executable procedure or executable application manipulates the UI display images in response to the signals received from the input devices. In this way, the user interacts with the display image using the input devices, enabling user interaction with the processor or other device.

Figure 1:
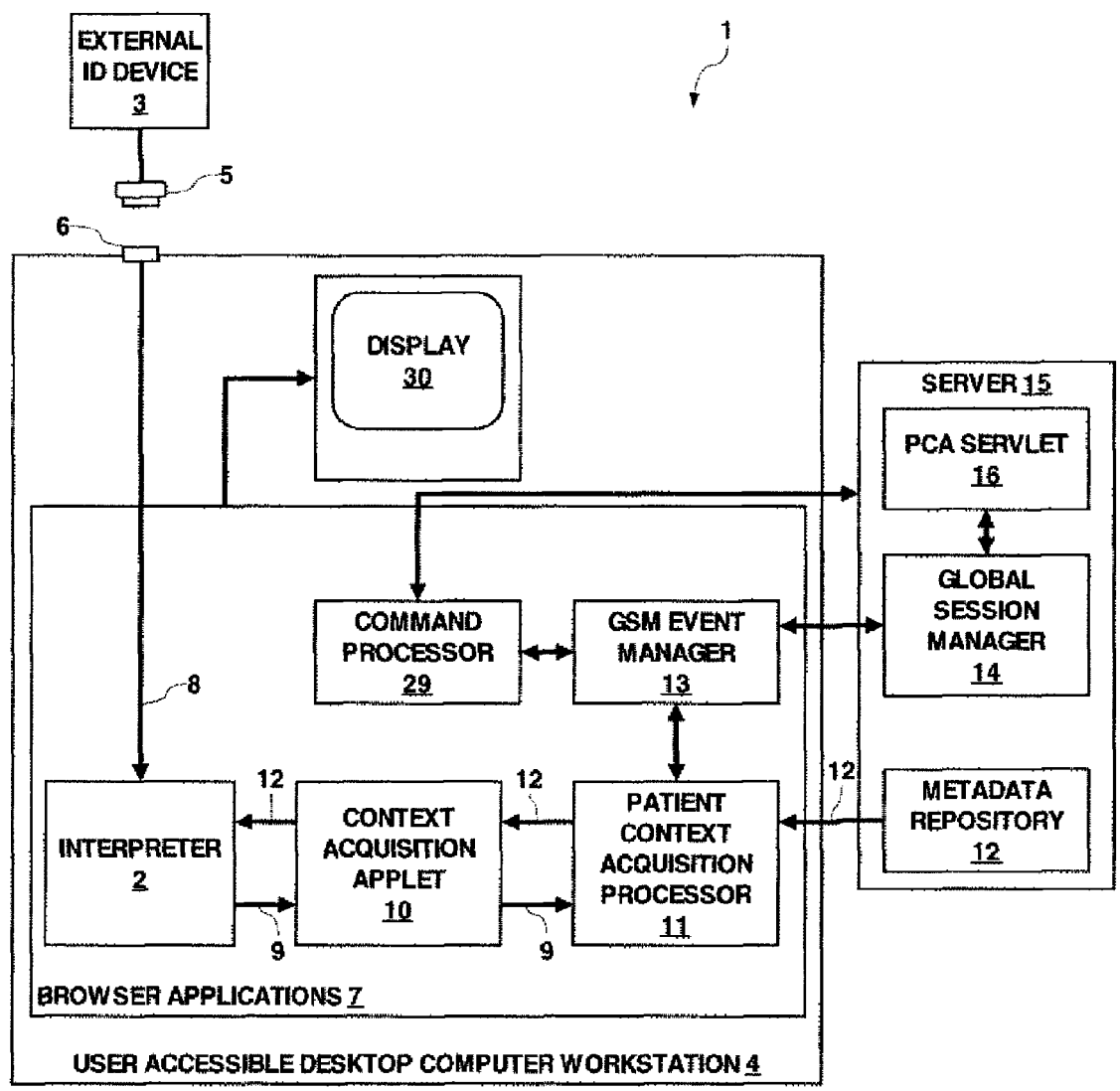
FIG. 1 is a block diagram of a medical information access and context processing system implemented according to the principles of the present invention.

A context acquisition processing system 1 illustrated in FIG. 1 addresses the need to utilize various otherwise incompatible scanning or reading devices 3 to capture various types of context information in different formats at a computer workstation 4. In general, a context acquisition processing system 1 is used for accessing medical data. The system includes an acquisition processor for acquiring configuration information indicating a type of a particular patient identification tag reader device 3 of a plurality of different types of tag reader devices and a format of patient identification data used by the particular patient identification tag reader device 3. An interpreter processes patient identification data received from the particular patient identification tag reader device 3 using the received configuration information to provide a particular patient identifier. A context processor updates a record indicating a current patient context. The patient context includes a patient identifier which is compatible with the particular patient identifier received from the tag reader device 3.

More specifically, the medical information access system 1 of FIG. 1 interfaces with a system user via the user accessible workstation computer workstation 4. System 1 provides adaptive patient selection using different technologies such as (a) a radio frequency identification (RFID) tags, (b) bar code labels, (c) wireless tags, (d) smart cards and/or (e) other similar types of technologies. The computer workstation 4 includes a processor, a display processor and display device 30, and a user interface (UI) comprising one or more display images enabling user interaction with a processor or other device. The computer workstation 4 further includes at least one browser compatible executable application 7. A worldwide-web-based executable application can be configured to utilize the system 1, and the software architecture permits the system 1 to seamlessly propagate different types of contextual information, in different formats, across multiple executable applications 7.

Figure 2:
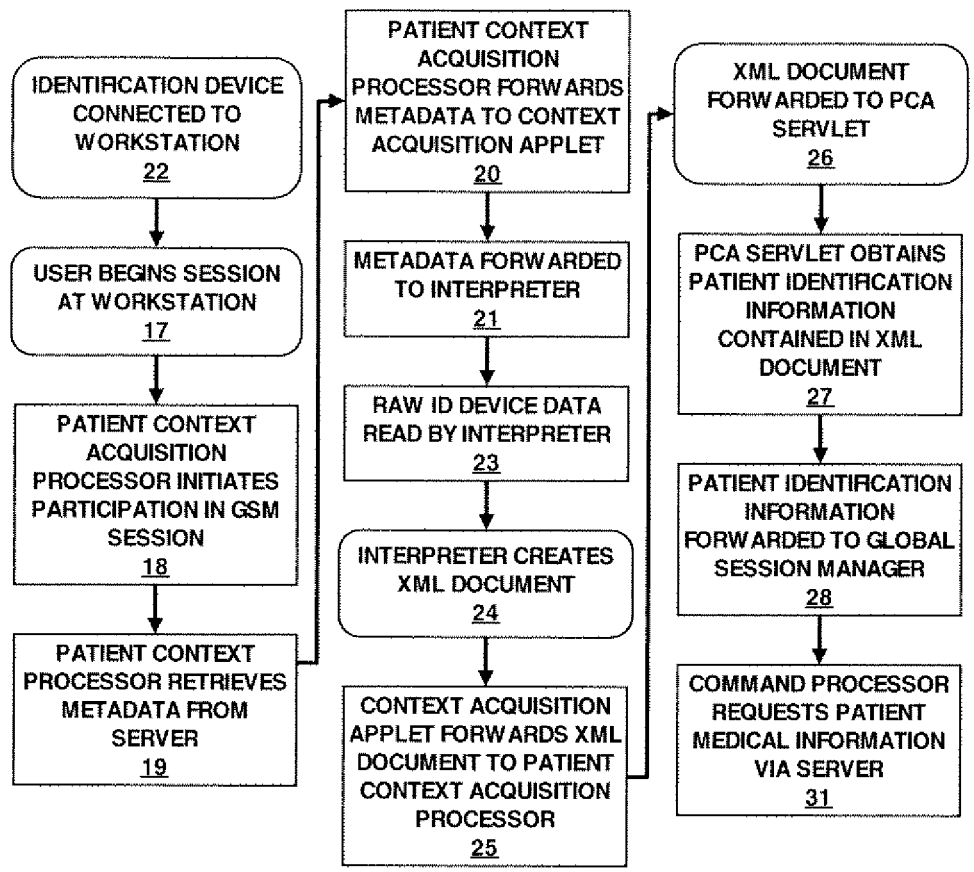
FIG. 2 is a flow chart describing operation of the system depicted in FIG. 1 according to principles of the present invention.

Referring concurrently to FIG. 1 and FIG. 2, the operation of the system 1 begins at block 22 (FIG. 2) in which an external identification reading or scanning device 3 (FIG. 1) is connected to the workstation 4. Referring to FIG. 1, the external device 3, is adapted to scan an identification tag attached to a patient. The external device 3, thus, obtains patient identification data and produces it in a standardized format. The workstation computer 4 is coupled to the external patient identification device 3 by means of a plug 5 and socket 6 or other suitable connection scheme (e.g., a wireless communication scheme). The socket 6 integrates with the computer workstation 4 as an input port, such as a serial data port. The computer workstation 4 subsequently reads raw data from the external device 3. The raw data 8 that is generated by the device 3 is forwarded to a clinical information systems context acquisition processor or interpreter 2.

In block 17 (FIG. 2) the user begins an identification data reading session. The interpreter 2 processes incoming data 8 read from the attached external device 3. In a preferred embodiment, the interpreter 2 communicates with the external device 3 that is connected to the end-user machine 4 by using standard Java application program interfaces (APIs) to read raw data 8 passing through the serial port formed by connectors 5 and 6. Java refers to the known Java software programming language. The data 8 obtained from the device 3 is processed and subsequently converted into extended markup language (XML) data 9 for subsequent processing.

The interpreter 2 is implemented as an ordinary Java object, sometimes referred to as a plain old Java object (POJO), to indicate that it does not follow any specified component architecture, conventions or frameworks. The interpreter 2 may be initialized to interact with an RFID object, a barcode object, or a smart card object, for example, based on the device 3 that is attached to the workstation 4. As reading of the device 3 is being performed by the interpreter 2, the interpreter 2 creates an XML document 9 containing data representing information received from the external device 3 which is forwarded to a context acquisition applet 10. The context acquisition applet 10 serves as the interface for the interpreter 2 in order to provide access between the interpreter 2 and other browser compatible executable applications 7.

The external devices 3 have the ability to receive data written on some form of media, and the interpreter 2 reads or captures this data. There exists today no standard format for the raw data 8 written and read by the various external scanning devices 3. In view of the lack of a single data format, the interpreter 2 acts as an interface and does not distinguish between the actual type of device 3 connected to the workstation 4. The interpreter 2 is a generic component, unaffected by the specific type of reader or scanner 3 attached to the computer 4. The interpreter 2 in the user accessible workstation is adapted to receive raw data 8 at the serial port connector 6 from the external identification device 3. The XML document 9 created by the interpreter 2 contains the patient identifying information as originally collected and subsequently transferred to the port 6 by the device 3.

The structure of the raw data 8 may utilize (a) fixed data positions, (b) field delimiters or (c) field names paired with field values and/or other data arrangement or protocol. Raw data 8 that utilizes fixed data positions may, for example, place the patient identifier (e.g. 23456) in bytes 1-10, the patient telephone number (e.g. 123-456-7890) at bytes 11-20, and continue with fixed data locations for all subsequent information.

Field delimited raw data 8 contains a specific byte that separates the individual data fields, and the fields themselves are placed in a particular order. For example, a byte having a value representing the character '|' may be used as the field delimiter with the first field being the patient identifier and the second field being the telephone number. The raw data 8 may in that case appear as 23456|123-456-7890|. The advantage of using field delimiters is that the raw data 8 does not have to be of a fixed length.

Paired raw data 8 is formatted by using data representing textual field names that are attached to or coupled with field values by a specific byte that separates the field names from associated field values. The same separator character may also separate successive data pairs, or a different character may be used for this purpose. For example, if the pair separator is the byte '=', the paired raw data might have the appearance of Patient ID=23456=Phone Nbr=123-456-7890=.

In order to accommodate the different data format or protocol standards, the interpreter 2 accesses predetermined basic knowledge of the raw data 8 such as, for example, the fact that a patient identifier is contained somewhere within a first predetermined number of bytes (e.g. ten bytes) of the data 8 as read from the serial port 6. The predetermined basic knowledge also includes, for example, the type of processing the interpreter 2 is to perform with the attached current reading or scanning device 3. This basic knowledge is represented by configuration data including metadata 12 and is used to overcome the lack of prior knowledge of the format of the raw data 8. The metadata 12 is maintained in a repository of metadata 12 including information regarding a method of raw data 8 transfer from the identification device 3 to the computer workstation 4, information regarding a structure of the raw data 8 transferred from the identification device 3 to the computer workstation 4, and information regarding the type of scanning device 3 connected to the computer workstation 4.

More specifically, in the illustrated embodiment, the configuration information includes metadata identifying a location of patient identification data in the raw data received from said particular patient identification tag reader device 3, and the plurality of different types of tag reader device comprise at least two of: (a) an RFID tag compatible reader device, (b) a bar code tag compatible reader device, and/or (c) a wireless tag compatible reader device. The interpreter 2 parses the patient identification data received from the tag or label reading device 3 in order to extract information containing the particular patient identifier, using the metadata identifying the location of that data The interpreter 2 may further recover other information contained within the raw data 8 such as, for example, the particular location of a patient encounter. In this case, the configuration information comprises metadata identifying a location of patient encounter identification data in the data received from the particular patient identification tag reader device 3.

In block 18 (FIG. 2), the patient context acquisition (PCA) processor 11 initiates a communication session with the server 15. In the illustrated embodiment, the PCA processor initiates a global session managed (GSM) session with the server 15. In block 19 (FIG. 2), a patient context acquisition (PCA) processor 11 retrieves metadata stored in a repository 12 in a server 15 and forwards it to a patient context acquisition applet 10 in block 20 (FIG. 2). The metadata 12 typically resides on a server machine 15 which acts as the centralized context information repository for the system 1. Such information may be accessed by various means, such as by the use of a universal resource locator (URL) request. The current patient context information contained within the metadata 12 is consequently made accessible by any of a number of executable applications that include the browser compatible executable applications 7.

In a preferred embodiment of the present invention, the centralized context information repository residing within server 15 and containing a patient context record (in a manner described in more detail below) is a repository used by a health level seven (HL7) application that is compatible with a global session manager (GSM) 14. Health level seven refers to the highest, or application, level as defined in the International Organization for Standardization (ISO) communications model for open systems interconnection (OSI). The application level addresses the definition of the data to be exchanged, the timing of the interchange, and the communication of certain errors to the application. Level seven supports such functions as security checks, participant identification, availability checks, exchange mechanism negotiations and, most importantly, data exchange structuring.

The metadata information 12 retrieved by the PCA processor 11 is accessible to a user as a web page appearing in a browser window, and contains preconfigured, site based information that specifies the type of Java object processor to be selected for use by interpreter 2 in order to accomplish the reception of data 8 based on site specific usage, namely, whether the device 3 that is in use at the site is RFID, barcode or smart card compatible. In some situations there may exist site-specific implementations for the writing of the context data by the device 3 to the specific storage media utilized. Further, at each site scanners or readers supplied by different vendors may be present, thus introducing the possibility of differing methods by which each vendor formats data to be written to the storage media.

In block 20 (FIG. 2), the context acquisition applet 10 interfaces with the PCA processor 11, obtaining the metadata information 12 and in block 21 (FIG. 2), the metadata information 21 is forwarded to the interpreter 2. The metadata includes data representing the type of Java object 2 to be initialized based on the type of device 3 attached to the workstation 4. In block 23 (FIG. 2), the interpreter 2 processes patient encounter identification data received from the particular patient identification tag reader device 3 using the received configuration information to provide a particular patient identifier. The interpreter 2 residing in the computer workstation 4 is adapted to receive the metadata 12, and is also adapted to receive the raw data 8 from the identification device 3.

The interpreter thereafter selects a raw data decoding protocol based on the metadata received by the interpreter. That is, the interpreter 2 receives raw data from the external patient identification device 3 and uses the supplied metadata 12 to interpret the raw data 8 and give it a usable meaning. The acquired metadata 12 includes first information regarding a method of raw data 8 transfer from the identification device 3 to the computer workstation 4 from the metadata repository 12. This first information indicates to the interpreter 2 that a particular type of a patient identification tag reader device 3 is connected to the computer workstation 4. The metadata 12 also contains second information regarding a structure of the raw data 8 transferred from the patient identification device 3 to the computer workstation 4 from the metadata repository 12. This second information indicates to the interpreter 2 a format of patient identification data used by said particular patient identification tag reader device 3 that is connected to the computer workstation 4. Thus, the specific device 3 that is attached to the user workstation 4 dictates both the device type and the expected structure of raw data 8. The metadata 12 contains the structural information associated with the raw data 8 that is to be read from the external device 3 including the data format as well as the location within the data stream of the patient identifier.

By describing the content of the raw data 8, the metadata 12 provides the interpreter 2 with the ability to obtain different types of context information contained within the data 8, including a patient identifier, an observation identifier or an encounter identifier such as a patient visit, phone call, inpatient stay or outpatient stay, for example. The interpreter 2 selects a raw data 8 decoding protocol based on the first and second information described above. The interpreter 2 uses the selected raw data decoding protocol to decode the raw data 8. For example, by using the metadata 12 to select the appropriate Java object for use by the interpreter 2, the applet 10 enables the interpreter 2 to perform an accurate interpretation of the raw data 8. In block 24 (FIG. 2), the interpreter 2 formulates the XML document 9 that is derived from the raw data 8 originally written to workstation 4 by the device 3. The patient identifier in the received raw data 8 is contained within the XML document. The interpreter 2 provides the XML document 9 to the context acquisition applet 10. In block 25 (FIG. 2), the context acquisition applet 10 forwards the XML document 9 containing the patient related data to the patient context acquisition (PCA) processor 11.

The PCA processor 11 also serves as an interface through which Global Session Manager (GSM) event manager 13 processes are executed. As part of the session initialization in block 18 (FIG. 2), the PCA processor 11 implements participation in the GSM session insofar as the processor 11 is a GSM compliant application and follows the GSM protocol. Once the GSM event manager is initiated, the web page created by the PCA processor 11 becomes an active desktop executable application 7. After the Java object selected for use by the interpreter 2 downloads the raw data 8 from the device 3 and subsequently performs the conversion into XML document 9, the PCA processor 11 is able to utilize the decoded patient information in the XML document 9 to make a request to the global session manager 14 to execute a patient context change. The PCA processor 11 issues either a patient context change request or a patient context verification message via the patient context acquisition processor or servlet 16 in server 15.

The PCA servlet 16 obtains the XML data 9 from the PCA processor 11 in block 26 (FIG. 2), and in block 27 (FIG. 2) the servlet 16 decodes the patient identifying information contained within the XML data 9. In block 28 (FIG. 2) the patient identification information is forwarded to the global session manager 14. This exchange of XML data 9, in which the servlet 16 functions as a context processor, results in an update, revision or verification of the patient context information; i.e. which patient is currently connected to the computer workstation 4.

The patient context information is a data record residing on the server 15 that indicates that the patient identifier is compatible with the patient identifier of the particular patient received from the tag reader device 3, and this context information is accessible by different executable applications. That is, the patient records (e.g. medical records) related to the patient identified by the patient identification information received from the patient identification device 3 are made available to the computer workstation 4 upon request by a browser compatible executable application 7. The context processor 11 updates a centralized context repository containing the record. The record indicates the current patient context accessible by a plurality of different browser compatible executable applications in the computer workstation 4.

Typically, the plurality of different browser compatible executable applications 7 are integrated with the GSM event manager 13 (FIG. 1). Such browser compatible executable applications 7 receive an event message from the GSM event manager 13 when the current patient context changes. When the browser compatible executable applications 7 receive such a message, they automatically synchronize to the new patient context. However, it is possible for the plurality of different browser compatible executable applications 7, and more specifically, those browser compatible executable applications 7 which are not integrated with the GSM event manager 13, to intermittently poll the record stored on server 15 in order to identify if the current patient context has changed. In response to such polling requests, the context processor 16 initiates generation of messages to the appropriate executable application indicating that: (a) the current patient context information has changed; or (b) that the current patient context information is compatible with the specific individual patient identifier received from the reader device 3.

In block 31 (FIG. 2), once the patient identification data is obtained and verified, a command processor executable application 29 incorporates the patient identifier into an application specific information access request directed to the server 15 in order to obtain medical information concerning the particular, identified patient and initiates display of an image including medical information of the particular patient. The information received by the command processor 29 is then available to the user of workstation 4 via display 30. The application specific information access request may employ a URL to make the request.

One skilled in the art understands that in one embodiment, the activities illustrated in FIG. 2 may be performed automatically. One skilled in the art further understands that in another embodiment, the individual activities illustrated in FIG. 2 may be performed in response to a user command.

The system 1 may also include a UI, utilizing the display processor and display device 30 for initiating generation of data representing a display image enabling user entry of the configuration information. In this manner, new or modified external patient identification devices 3 may be implemented without changes to the executable applications. Instead, only the metadata describing the new or revised location and format of the patient identification information from the patient identification device 3 needs to be updated.

Although the present invention has been described with a degree of particularity, the embodiments described are exemplary only and numerous variations of the invention are possible. In particular, the architecture of the system 1 provides an extensible interface that is able to accommodate different kinds of external context data devices 3. This extensibility allows a user of the system 1 to obtain a host of contextual information while providing a seamless workflow from the reading of the device 3 through retrieval of context information. An alternative embodiment of the present invention combines the clinical information system context acquisition processor or interpreter 2 and the patient context acquisition processor 11 into a single implementation. The system 1 is not limited to the field of healthcare and can be used in any data processing situation involving context information selection such as, for example, inventory processing. The system 1 is also usable by a mobile user providing care at the patient bedside.

What is claimed is:

1. A context information processing system used for accessing medical data, comprising:
    an acquisition processor for acquiring configuration information indicating a type of a particular patient identification tag reader device for a plurality of different types of tag reader device and a format of patient identification data used by said particular patient identification tag reader device;
    an interpreter for using the acquired configuration information in selecting a data decoding protocol from a plurality of different decoding protocols used for decoding data from a corresponding plurality of different types of patient identification tag reader device and using the selected decoding protocol for processing patient identification data received from said particular patient identification tag reader device using said acquired configuration information to provide a particular patient identifier; and
    a context processor for updating a record indicating a current patient context comprising a patient identifier to be compatible with said particular patient identifier.

2. A system according to claim 1, wherein:
    said context processor updates a centralized context repository containing said record; and
    said record indicating said current patient context is accessible by a plurality of different executable applications.

3. A system according to claim 2, wherein said plurality of different executable applications intermittently poll said record indicating said current patient context to identify that said current patient context has changed.

4. A system according to claim 2, wherein said centralized context repository containing said record comprises a repository used by an HL7 compatible Global Session Manager (GSM) application.

5. A system according to claim 1, wherein said context processor initiates generation of a message to an executable application indicating at least one of, (a) said current patient context has changed and (b) said current patient context comprising said patient identifier compatible with said particular patient identifier.

6. A system according to claim 1, wherein said interpreter processes patient encounter identification data received from said particular patient identification tag reader device using said acquired configuration information to provide a particular patient identifier.

7. A system according to claim 1, wherein:
said configuration information comprises metadata identifying a location of patient identification data in said data received from said particular patient identification tag reader device; and
said plurality of different types of tag reader device comprise at least two of: (a) an RFID tag compatible reader device, (b) a bar code tag compatible reader device, and (c) a wireless tag compatible reader device.

8. A system according to claim 7, wherein said interpreter parses said patient identification data received from said particular patient identification tag reader device to extract information comprising said particular patient identifier using said metadata identifying said location.

9. A system according to claim 1, wherein said configuration information comprises metadata identifying a location of patient encounter identification data in said data received from said particular patient identification tag reader device.

10. A system according to claim 1, further comprising:
a command processor for incorporating said particular patient identifier in an application specific information access request to obtain medical information concerning said particular patient and initiating display of an image including medical information of said particular patient.

11. A system according to claim 1, wherein said application specific information access request employs a URL.

12. A system according to claim 1, further comprising a display processor for initiating generation of data representing a display image enabling user entry of said configuration information.

13. A medical information access system, comprising:
a user accessible workstation adapted to receive raw data from a plurality of different types of patient identification tag reader device;
a repository of metadata, the metadata comprising:
information regarding a plurality of methods of raw data transfer from a corresponding plurality of patient identification tag reader devices to the workstation, and
information regarding a plurality of structures of the raw data provided by said plurality of patient identification tag reader devices; and
an interpreter, the interpreter residing within the workstation and being adapted to receive the metadata, the interpreter selecting a raw data decoding protocol from a plurality of different decoding protocols used for decoding data from a corresponding plurality of different types of patient identification tag reader device based on the metadata received by the interpreter and using the selected decoding protocol in decoding the received raw data.

14. The medical information system of claim 13 wherein the metadata contains information indicating to the interpreter that a particular type of a patient identification tag reader device is connected to the workstation.

15. The medical information system of claim 14 wherein the metadata includes information indicating to the interpreter a format of patient identification data used by said particular patient identification tag reader device that is connected to the workstation.

16. The medical information system of claim 15 further comprising a context processor for updating a record indicating that a current patient context comprising a patient identifier is compatible with a particular patient identifier.

17. The medical information system of claim 16, wherein said context processor updates a centralized context repository containing said record.

18. A method of accessing and processing medical identification data, comprising:
using a workstation coupled to a device adapted to scan an identification tag, the workstation reading raw data from the device adapted to scan an identification tag and being used for,
acquiring first information regarding a method of raw data transfer from the identification device to the workstation from a repository of said first information;
acquiring second information regarding a structure of the raw data transferred from the device to the workstation from a repository of said second information;
selecting a raw data decoding protocol from a plurality of different decoding protocols used for decoding data from a corresponding plurality of different types of identification tag reader device in response to the acquired first information; and
decoding the raw data using the selected raw data decoding protocol.

19. The method of claim 18, further comprising formulating an XML document derived from the decoded raw data.

20. The method of claim 19, further comprising identifying a particular patient identifier contained within said XML document.

* * * * *